(12) United States Patent
Stephens, II et al.

(10) Patent No.: US 10,346,962 B2
(45) Date of Patent: Jul. 9, 2019

(54) NONDESTRUCTIVE METHOD TO PREDICT ISOSTATIC STRENGTH IN CERAMIC SUBSTRATES

(75) Inventors: Alan Thomas Stephens, II, Beaver Dams, NY (US); Leon Robert Zoeller, III, Hammondsport, NY (US)

(73) Assignee: Corning Incorporated, Corning, NY (US)

(*) Notice: Subject to any disclaimer, the term of this patent is extended or adjusted under 35 U.S.C. 154(b) by 1577 days.

(21) Appl. No.: 13/370,993

(22) Filed: Feb. 10, 2012

(65) Prior Publication Data

US 2013/0212051 A1     Aug. 15, 2013

(51) Int. Cl.
| | |
|---|---|
| *G06K 9/66* | (2006.01) |
| *G06N 3/02* | (2006.01) |
| *G06T 7/00* | (2017.01) |
| *G01N 21/956* | (2006.01) |

(52) U.S. Cl.
CPC ..... *G06T 7/0004* (2013.01); *G01N 21/95692* (2013.01); *G06K 9/66* (2013.01); *G06N 3/02* (2013.01); *G06K 2209/19* (2013.01); *G06T 2207/20084* (2013.01); *G06T 2207/30164* (2013.01)

(58) Field of Classification Search
CPC ................................ G06T 7/0004; G06N 3/02
USPC .......................................................... 706/16
See application file for complete search history.

(56) References Cited

U.S. PATENT DOCUMENTS

| | | | |
|---|---|---|---|
| 4,064,534 A | 12/1977 | Chen et al. ................... 358/107 |
| 4,926,350 A | 5/1990 | Bechtel et al. ............... 364/550 |
| 5,748,322 A | 5/1998 | Konder et al. ................ 356/394 |
| 6,567,162 B2 | 5/2003 | Koren et al. ................ 356/237.2 |
| 6,938,409 B2 | 9/2005 | Birckigt et al. ................ 60/275 |
| 6,959,104 B2 | 10/2005 | Rajagopal et al. ........... 382/107 |
| 7,472,097 B1* | 12/2008 | Scarborough et al. ......... 706/26 |
| 7,655,195 B1* | 2/2010 | Ichikawa ........... B01D 46/2451 422/180 |
| 7,680,304 B2 | 3/2010 | Biernacki et al. ............ 382/108 |
| 8,051,703 B2 | 11/2011 | Poff et al. ......................... 73/37 |
| 2006/0151926 A1* | 7/2006 | Zoeller, III ................... 264/603 |

(Continued)

FOREIGN PATENT DOCUMENTS

CN      201047836      4/2008

OTHER PUBLICATIONS

Yeh, I-C. "Modeling of strength of high-performance concrete using artificial neural networks." Cement and Concrete research 28.12 (1998): 1797-1808.*

(Continued)

*Primary Examiner* — Scott A. Waldron
*Assistant Examiner* — Kevin W Figueroa

(57) ABSTRACT

A method of examining a cellular structure includes the steps of providing an inspecting device, a neural network and a target cellular structure that includes a plurality of target cells extending therethrough and further includes a target face exposing an arrangement of the target cells; inspecting the arrangement of cells on the face of the target cellular structure using the inspecting device; representing the arrangement of cells with numerically defined target cell parameters; inputting the target cell parameters into the neural network; and generating an output from the neural network based on the target cell parameters, the output being indicative of a strength of the target cellular structure.

17 Claims, 5 Drawing Sheets

(56) References Cited

U.S. PATENT DOCUMENTS

| | | | |
|---|---|---|---|
| 2009/0110829 A1* | 4/2009 | Johnson | B41J 3/01 |
| | | | 427/256 |
| 2009/0239028 A1 | 9/2009 | Ohno et al. | 428/116 |
| 2010/0165340 A1* | 7/2010 | Xu et al. | 356/327 |
| 2010/0208039 A1 | 8/2010 | Stettner | 348/49 |
| 2010/0218596 A1* | 9/2010 | Poff et al. | 73/37 |
| 2011/0116704 A1 | 5/2011 | Zoeller, III | |
| 2011/0240190 A1* | 10/2011 | Summers et al. | 152/151 |

OTHER PUBLICATIONS

Abstract: Anon Source: Automotive Engineering International, "Hot vibration durability of ceramic preconverters", v 104, n 3, p. 43-47, Mar 1996; Publisher: SAE.

Abstract: Brill, U.; Heubner, U., "Materials for metal carriers of automobile exhaust catalytic converters", Source: Stahl und Eisen, n Spec Is, p. 134-135, Sep. 14, 1990.

Abstract: Chen, David K.S.; Verma, Anil, "Integrity of an automotive catalytic converter during the assembly process", Source: American Society of Mechanical Engineers (Paper), 1990; Conference: Proceedings of the Winter Annual Meeting, Nov. 25, 1990-Nov. 30, 1990.

Abstract: Chen, David K.S., "Mechanical behavior and strength of honeycomb ceramic cellular substrates. A microscopic view", Source: American Society of Mechanical Engineers (Paper), 1990; Conference: Proceedings of the Winter Annual Meeting, Nov. 25, 1990-Nov. 30, 1990.

Abstract: Clauss, B.; Schawaller, D., "Modern aspects of ceramic fiber development", Source: Advanced Inorganic Fibrous Composites V, 9-16, 2006; Conference: Advanced Inorganic Fibrous Composites V, Jun. 4-9, 2006, Sicily, Italy.

Abstract: Gulati, Suresh T.; Reddy, K.P., "Size effect on the strength of ceramic catalyst supports", Source: SAE Special Publications, n 938, p. 129-134, 1992, Automotive Emissions and Catalyst Technology; Conference: International Fuels and Lubricants Meeting and Exposition, Oct. 19, 1992-Oct. 22, 1992.

Abstract: Gulati, S.T., "Thermomechanical properties of washcoated ceramic catalyst supports", Source: Industrial Ceramics, v 22, n 1, p. 49-54, Jan./Apr. 2002.

Abstract: Locker, Robert J.; Sawyer, Constance B.; Schmitt, Paul S., "Demonstration of high temperature durability for oval ceramic catalytic converters-2", Source: SAE Special Publications, v 1335, p. 7-12, Feb. 1998, General Emissions; Conference: Proceedings of the 1998 SAE International Congress & Exposition, Feb. 23, 1998-Feb. 26, 1998.

Abstract: Maattanen, Mauri; Lylykangas, Reijo, "Mechanical strength of a metallic catalytic converter made of precoated foil", Source: SAE Special Publications, n 810, p. 71-79 900505, Feb. 1990; Conference: Electronic Diesel Engine Controls—Papers presented at the 1990 SAE International Congress and Exposition, Feb. 26, 1990-Mar. 2, 1990.

Abstract: Wang, Zhong-Minl; Lin, Y.S., "Sol-gel-derived alumina-supported copper oxide sorbent for flue gas desulfurization", Source: Industrial and Engineering Chemistry Research, v 37, n 12, p. 4675-4681, Dec. 1998.

* cited by examiner

NONDESTRUCTIVE METHOD TO PREDICT ISOSTATIC STRENGTH IN CERAMIC SUBSTRATES

TECHNICAL FIELD

The present disclosure relates to neural networks and, more particularly, methods of using a neural network to predict the strength of structures with cells.

BACKGROUND

Honeycomb cellular structures are used in vehicular exhaust systems to reduce pollutants. Such structures are generally formed by extrusion and comprise a network of interconnected web walls that form a matrix of elongated, gas-conducting cells which may be square, octagonal, hexagonal, or the like. In some examples, the network of web walls may be surrounded by a cylindrical outer skin that is integrally connected to the outer edges of the web walls to form a cylindrical structure having opposing inlet and outlet end faces for receiving and expelling exhaust gases through the matrix of cells.

Honeycomb cellular structures are typically inspected to ensure they meet specifications for cell shape, cell size, web-wall thickness, skin integrity, etc., and to ensure they are free of defects. However, given the large number of cells, it takes a significant amount of time to inspect a single honeycomb cellular structure using inspection methods and systems known in the art. Moreover, the honeycomb cellular structure may be subjected to certain operating conditions under which it must withstand high levels of pressure or force. The pressure that honeycomb cellular structure can withstand is conventionally determined by destroying the structure and results in a wasted part. Moreover, the destroyed honeycomb cellular structure might not correctly predict the strength of a different cellular structure which may have minute structural differences that are hard to observe. Therefore, a need exists for a method and an apparatus that can quickly perform inspection on a ceramic honeycomb structure and predict at the manufacturing stage whether the ceramic honeycomb structure can withstand high levels of pressure or force without destruction of the honeycomb structure.

SUMMARY

In one example aspect, a method of examining a cellular structure includes the steps of providing an inspecting device, a neural network and a target cellular structure that includes a plurality of target cells extending therethrough and further includes a target face exposing an arrangement of the target cells; inspecting the arrangement of cells on the face of the target cellular structure using the inspecting device; representing the arrangement of cells with numerically defined target cell parameters; inputting the target cell parameters into the neural network; and generating an output from the neural network based on the target cell parameters, the output being indicative of a strength of the target cellular structure.

In one example of the example aspect, a method of examining a cellular structure includes the steps of: providing an inspecting device, a storage medium, a plurality of sample cellular structures and a neural network, each of the sample cellular structures including a plurality of sample cells extending therethrough and further including a sample face exposing an arrangement of the sample cells; inspecting the arrangement of sample cells on the sample face of each of the sample cellular structures using the inspecting device; representing the arrangement of sample cells of each of the sample cellular structures with numerically defined sample cell parameters; applying force on each the sample cellular structures while measuring a sample strength parameter representing a maximum force the sample cellular structure can endure prior to destruction; storing in the storage medium the sample cell parameters and the sample strength parameter corresponding to each of the sample cellular structures so as to obtain a sample database; and inputting the sample cell parameters and the sample strength parameter stored in the storage medium into the neural network such that the neural network can detect a relationship between the sample strength parameter and the sample cell parameters based on the sample database.

BRIEF DESCRIPTION OF THE DRAWINGS

These and other aspects are better understood when the following detailed description is read with reference to the accompanying drawings, in which.

DETAILED DESCRIPTION

Figure 1:
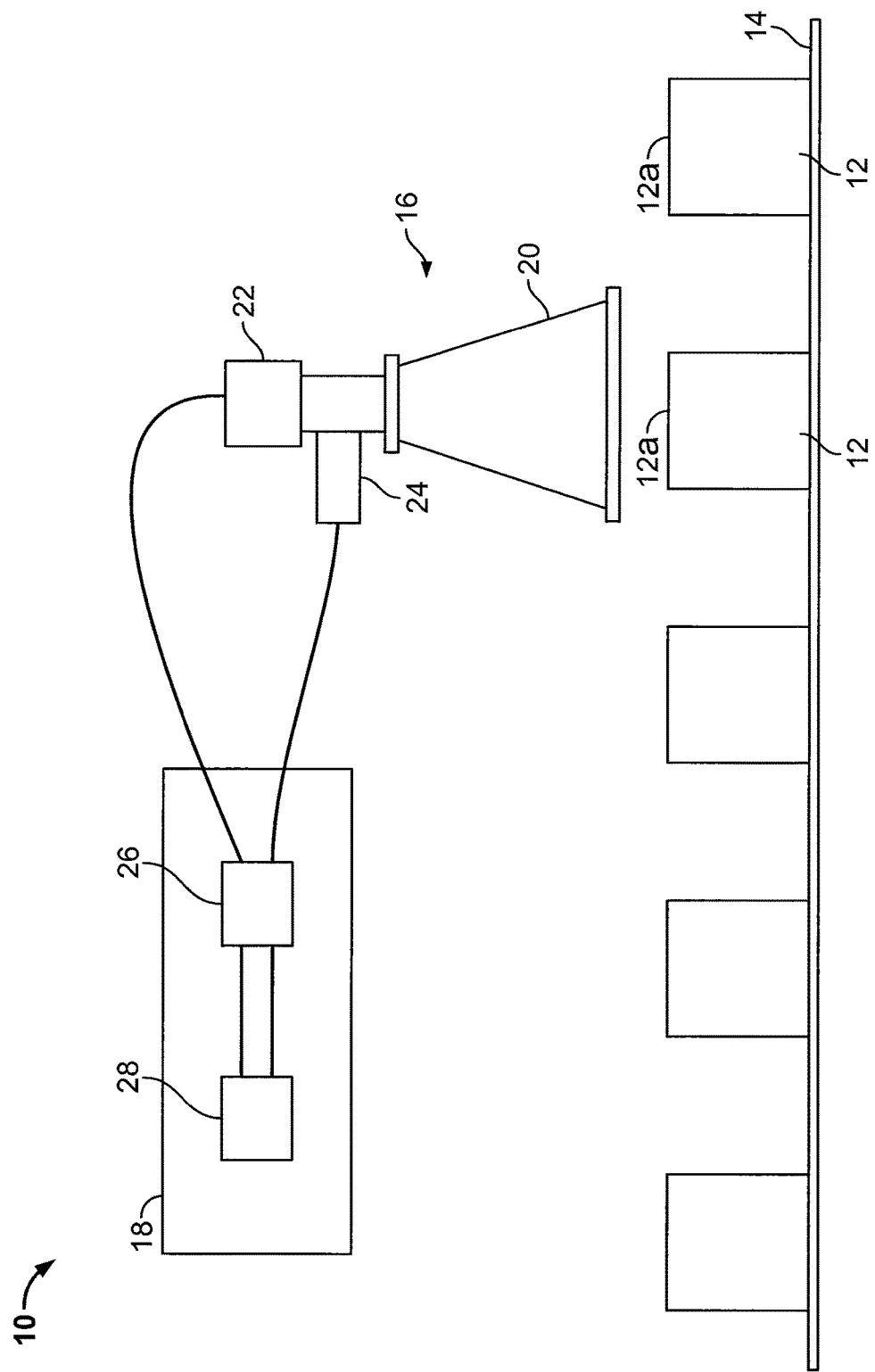
FIG. 1 is a schematic view of an example embodiment of a system configured to examine a cellular structure.

Examples will now be described more fully hereinafter with reference to the accompanying drawings in which example embodiments are shown. Whenever possible, the same reference numerals are used throughout the drawings to refer to the same or like parts. However, aspects may be embodied in many different forms and should not be construed as limited to the embodiments set forth herein.

Example embodiments of apparatus and methods of examining a cellular structure are provided. Cellular structures can comprise various cellular structure configurations for different applications. For example, the cellular structures can comprise honeycomb cellular structures for vehicular exhaust applications. For instance, the cellular structure can comprise a ceramic honeycomb substrate that can be used to receive a washcoat of a catalytic agent to reduce hydrocarbon emissions in a vehicular exhaust system. In addition or alternatively, the ceramic honeycomb substrate may comprise porous walls to allow the honeycomb cellular structure to remove particulates from the vehicle exhaust stream.

As shown in FIG. 1, an example embodiment of a system 10 configured to examine a cellular structure 12 is shown. The system 10 may include a conveyor 14, an inspecting device 16 and a processing device 18 (e.g., a computer). The cellular structures 12 may be made of moldable material such as ceramic and may be manufactured through a variety of methods including an extrusion process. The cellular structures 12 may include a plurality of cells 12b (FIG. 4) that extend therethrough and may include a face 12a that may be located at an end and exposes an arrangement of the cells. The cellular structures 12 may be placed on the conveyor 14 with the face 12a oriented toward the inspecting device 16. The conveyor 14 may transport a plurality of cellular structures 12 along a belt such that each cellular structure 12 passes underneath the inspecting device 16 and each cellular structure 12 may come to a stop when located directly under the inspecting device 16.

The inspecting device 16 may include a lens 20, a charge-coupled device (CCD) camera 22 and an illuminator 24. The lens 20 may be configured to magnify the face 12a of the cellular structure 12 for close-up inspection of the arrangement of the cells 12b while the illuminator 24 may be configured to flash light as an image of the face 12a is taken by the CCD camera 22. The CCD camera 22 may scan the face 12a of the cellular structures 12 by taking composite line images of the face 12a. The inspecting device 16 thereafter transmits the image of the face 12a to the processing device 18 which may include a storage medium 26 where the image may be stored and/or processed and a neural network 28.

In one set of example operations, the processing device 18 may signal the illuminator 24 to strobe light onto the face 12a of the cellular structure 12 thereby freezing the motion of the cellular structure 12 that is moving on the conveyor 14. The CCD camera 22 captures an image which is transmitted to the storage medium 26. The processing device 18 may analyze every cell in the image generating a vector of measurements and may organize the information about each cell into rows and columns.

Figure 2:
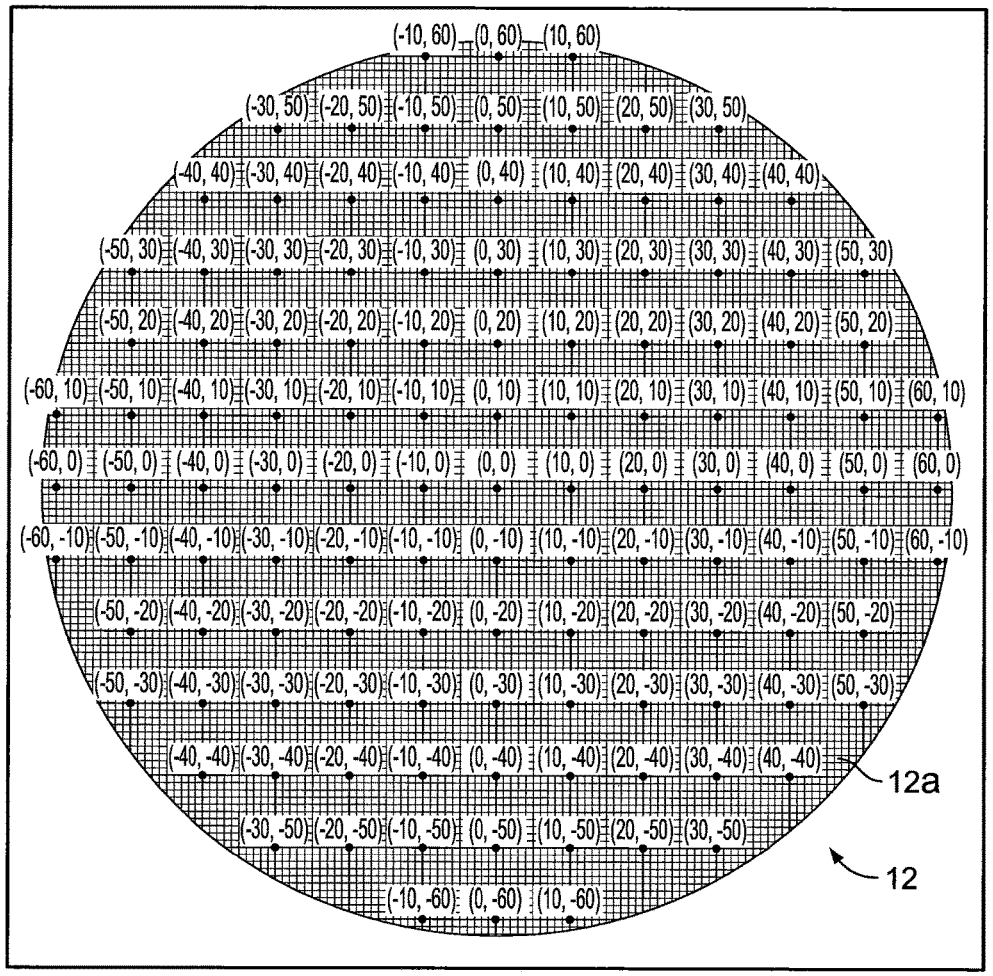
FIG. 2 is a first image of a face of the cellular structure which is captured by the system and in which cells are detected at every first interval.
Figure 3:
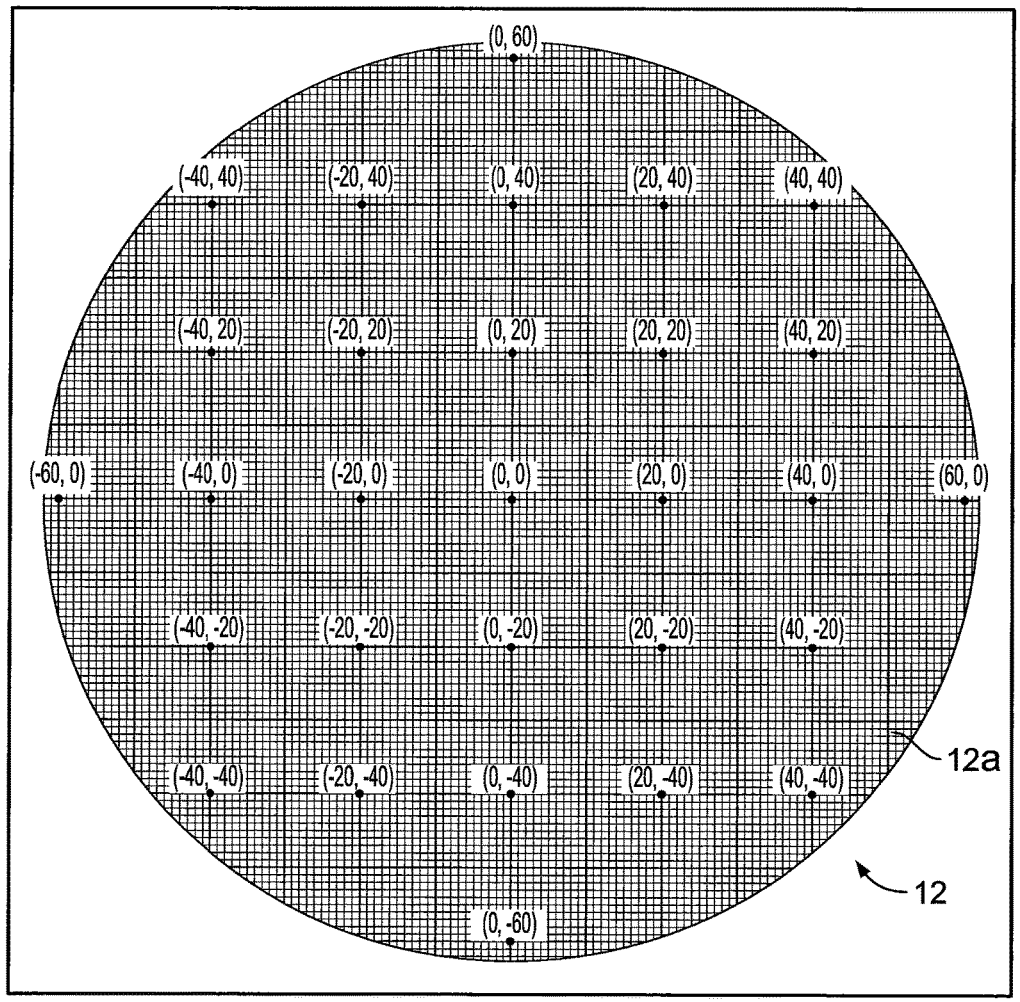
FIG. 3 is a second image of the face of the cellular structure which is captured by the system and in which the cells are detected at every second interval.

The processing device 18 can detect and indicate the locations of the cells 12b with a set of Cartesian coordinates. The processing device 18 may be configured to detect every nth cell spaced apart at regular intervals along rows and columns rather than every single cell on the face 12a of the cellular structure 12. Information relating to every single cell on the face 12a may be more than necessary and may cause delay of operations. For example, FIG. 2 shows every tenth cell along rows and columns as measured from an origin (i.e., (0,0)), located at the center of the face 12a, and FIG. 3 shows every twentieth cell along rows and columns as measured from the origin. The density of the cells that are detected by the processing device 18 may change depending on the amount of information that will be provided to the neural network 28. Based on a comparison between the actual locations of the cells 12b (see FIG. 4) relative to the origin and the optimal locations of the cells 12b relative the origin, it is possible to determine the deviations and distortions in the arrangement of the cells 12b.

Figure 4:
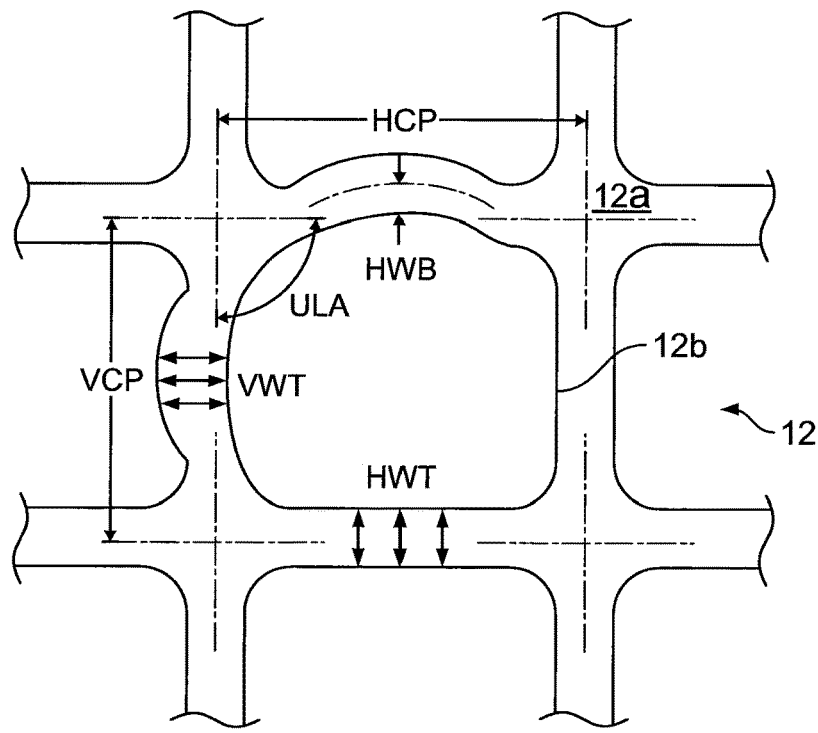
FIG. 4 is a close up view of a cell in an image of the face of the cellular structure captured by the system.

Moreover, as shown in FIG. 4, there are other cell parameters that the processing device 18 can detect through a close-up inspection of the image of the face 12a such as cell corner angles (e.g., upper left angle (ULA)), cell pitches (e.g., horizontal cell pitch (HCP) or vertical cell pitch (VCP)), wall thicknesses (e.g., vertical wall thickness (VWT) or horizontal wall thickness (HWT)), and wall bows (e.g., horizontal wall bow (HWB) or vertical wall bow (VWB)). Further details relating to the inspecting device 16 and cell parameters obtained using the inspecting device 16 are described in application Ser. No. 12/617,778, filed Nov. 13, 2009, which is incorporated herein by reference in its entirety.

With regard to cell corner angles, while information concerning all four of the cell angles is available, only one cell angle per cell is needed to characterize the angular information for a given cell. Note that square cell 12b contains four angles so that all of the angles must add up to 360 degrees. Typically, the angles at the opposite corners of cell 12b are equal and the other two angles are approximate complementary angles, thereby allowing for just one cell angle for cell characterization. Horizontal cell pitch or HCP generally measures the difference in the X-coordinates of cell corners. While each cell 12b includes two such cell pitches (upper and lower), only one such measurement is needed for most applications. In an example embodiment, an average of the upper and lower horizontal cell pitch HCP is used. Note also that the bottom HCP is the same as the top HCP of the cell directly below so that no information is lost. Vertical cell pitch generally measures the difference in the Y-coordinates of cell corners. As is the case with the horizontal cell pitch HCP, while each cell includes two vertical cell pitches (upper and lower), only one such measurement is needed for most applications. In an example embodiment, an average of the left and right vertical cell pitch VCP is used. Note also that the right VCP is the same as the left HCP of the cell directly to the right so that no information is lost. Horizontal wall thickness or HWT measures the location of the top and bottom edges of the top horizontal web wall and subtracting the two locations. An example of this calculation is carried out for each set of 5 μm pixels that compose the top and bottom edges of web wall. Once the differences are calculated (this may produce between 100 and 300 thickness measurements, depending on the size of cell 12b), they are averaged to produce an average thickness. Vertical wall thickness or VWT is calculated in an analogous manner to the horizontal wall thickness HWT. Horizontal wall bow or HWB measures the center point of the top horizontal web wall. This center point is defined as the midway point between the two top corners of the cell 12b and the midway point of the top of the web wall and the bottom of the web wall at the location of the midway point. A second point is found by drawing a line between the two top corner points of the cell and finding the center point of this line. The horizontal wall bow is the difference in the X-direction between these two points. The web wall can bow into the cell or away from the cell. If the bow projects into the cell its value is negative, and if it projects out from the cell it is positive. The vertical wall bow or VWB is calculated in an analogous manner to the horizontal wall bow. Another perimeter detected by the processing device 18 may include a perimeter or outer skin of the face 12a which can be defined by a best-fit shape (e.g., a circle, an oval, etc.) and which can be used to find a geometric center of the face 12a. A shape vector may define in polar coordinates the deviation from the actual perimeter shape to the best-fit perimeter shape. Yet another perimeter detected may be the thickness of the outer skin of the face 12a. A thickness may be defined by measuring the variation in skin thickness by subtracting from the outer skin radius the inner skin radius at various angles around the skin.

In order to determine the parameters indicated on FIG. 4, it may be necessary to first find the center of the face 12a based on the best-fit perimeter shape and then find best-first vertical and horizontal centerlines that form an idealized or reference web including the best-fit web intersections corresponding to corners of an idealized cell 12b.

Moreover, in certain cases to be discussed below, another cell parameter that is indicative of an isostatic strength of the cellular structure 12 can be measured. In one example setting to measure the isostatic strength of a cellular structure 12, the cellular structure 12 can be submerged in a liquid and the pressure of the liquid can be gradually increased until the cellular structure 12 cannot withstand the pressure and is destroyed such as by cracking or imploding. The maximum pressure or force endured by the cellular structure 12 can be measured and used as a strength parameter of the cellular structure 12.

All of these cell parameters can be defined numerically such that one set of numerical values corresponding to the aforementioned cell parameters can be obtained after scanning the face 12a of each cellular structure 12. Moreover, the numeral values corresponding to the cell parameters can be stored in the storage medium 26.

Figure 5:
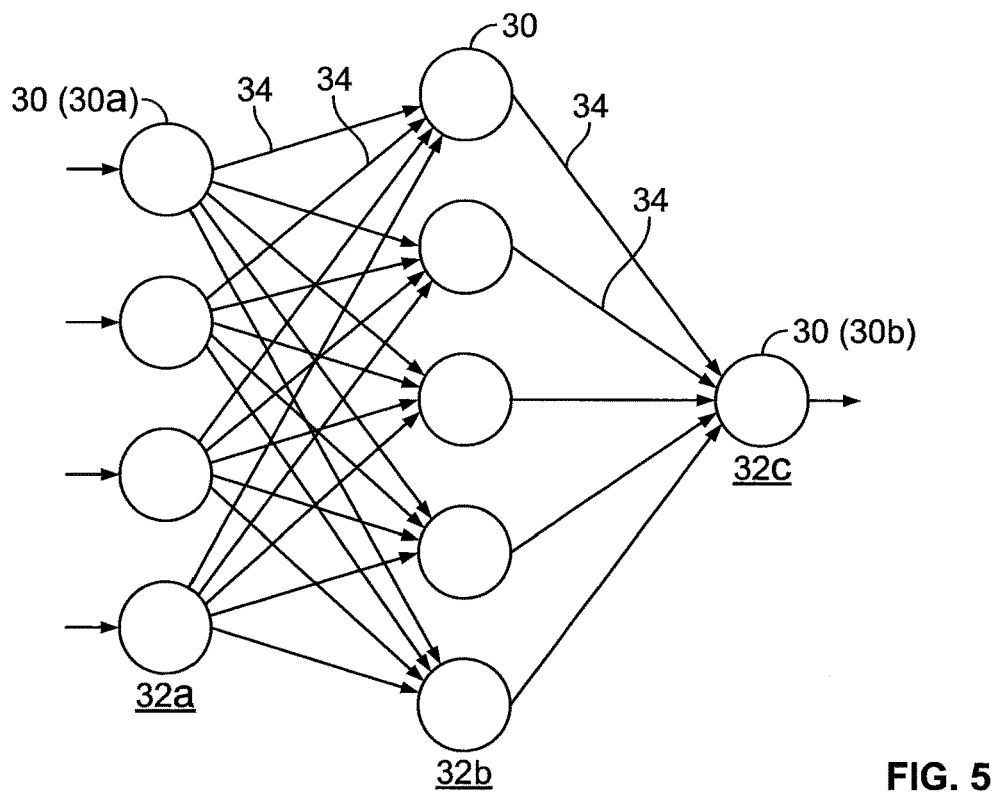
FIG. 5 is a schematic representation of an operation of an example embodiment of a neural network.

As shown in FIG. 5, the neural network 28 of the processing device 18 may process information through an interconnected group of artificial neurons 30. An example embodiment of the neural network 28 is shown schematically in FIG. 5 and has three layers 32a, 32b, 32c of neurons 30. The first layer 32a has input neurons 30a that send information by way of synapses 34 to the second layer 32b of neurons 30 and then to the third layer 32c of output neurons 30b. Manipulation of the information occurs by altering weights which are parameters stored at the synapses 34. The neural network 28 has the capability to learn such that, if given a specific task to solve and a class of functions, the neural network 28 is able to solve the task in some optimal sense by observing the information transmitted through the neurons 30.

Figure 6:
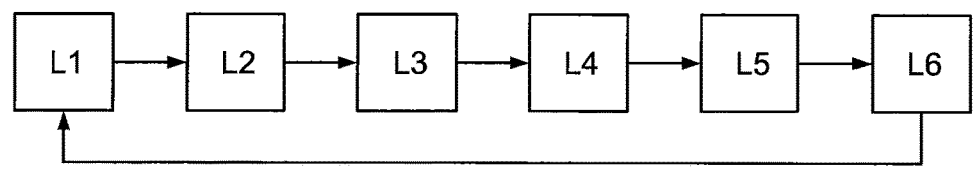
FIG. 6 is a flow chart representing multiple operating steps during a learning mode of the system.

Referring to FIG. 6, the aforementioned learning capability of the neural network 28 can be put to use by configuring the system 10 into a learning mode in which the neural network 28 detects or hypothesizes a relationship between the strength parameter and the cell parameters. In an example embodiment, the face 12a of a sample cellular structure 12 is captured as an image or scanned by the inspecting device 16 (step L1) and is turned into a set of numerical values representing the sample cell parameters (step L2). Then, the strength of the sample cellular structure 12 is measured during the above-mentioned destruction process and is represented as the sample strength parameter (step L3). The cell parameters and the strength parameters obtained from the sample cellular structure 12 are stored in storage medium 26 (step L4) and are input into the neural network 28 (step L5). The neural network 28 hypothesizes a relationship between the strength parameter and the cell parameters by observing the values of the strength parameter and the cell parameters obtained from the sample cellular structure 12 (step L6). Thereafter, these steps are repeated so that the neural network 28 can observe the values in a sample database containing the strength parameter and the cell parameters obtained from a plurality of sample cellular structures 12. The sample database may be formed from cell parameters and strength parameters obtained from a large pool of sample cellular structures. The relationship detected by the neural network 28 is likely to be more reliable with a larger the pool of sample cellular structures 12. It may be possible to first form a sample database by gathering the cell parameters and the strength parameters from the pool of sample cellular structures 12 and provide the parameters to the neural network 28 at once.

The neural network 28 may determine, for example, that a few of the aforementioned cell parameters play predominant roles in deciding the strength parameter of the cellular structure 12 and that the strength parameter is proportional to each of these cell parameters. The neural network 28 may generate multiple neural net models each of which has a different set of weights for each of the synapses in the neural net model. Out of the multiple neural net models, the neural net model with the best accuracy can be generated as a program in C code which can then be used to predict the isostatic strength of the cellular structures 12.

However, due to the unclear nature of neural networks 28, which imitate the functioning of the neurons in the human brain, it may not be possible to unambiguously express the relationship detected by the neural network 28 in mathematical terms, algorithmic terms, or other terms of notations commonly used in other fields of art. Thus, the terms "hypothesize" or "detect", which are used to describe the function of the neural network 28 recognizing a relationship between the strength parameter and the cell parameters, should not be construed to necessarily mean that the relationship is definable without uncertainty, that the relationship is expressible with notations commonly used in various fields of art or that the relationship is perceptible by the human brain.

A person of ordinary skill in the art will understand and recognize that some lack of clarity is unavoidable in using a neural network 28 but that the capabilities of the neural network 28 can still be put to use despite a failure to completely understand how the neural network 28 determined the relationship or obtained an output. Thus, despite the unclear nature of the relationship, the relationship detected by the neural network 28 may be used to yield an output value that can be used to determine whether or not the cellular structure 12 is suitable for use in a given environment (e.g., vehicular exhaust systems). While the output value may be a numerical prediction of the strength of the target cellular structure 12, the output value may also be expressed in terms of "pass" or "fail" indicating whether or not the cellular structure 12 can endure the pressures or forces in a given set of operation conditions.

Figure 7:
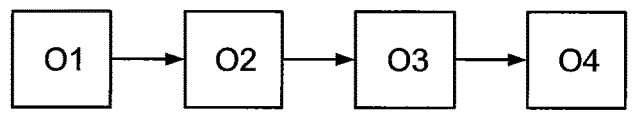
FIG. 7 is a flow chart representing multiple operating steps during a predicting mode of the system.

Moreover, after the neural network 28 has detected a relationship between the strength parameter and the cell parameters, the system 10 can be configured into a predicting mode in which the strength of a target cellular structure 12 is predicted after inspecting the face 12a of the cellular structure 12 as shown in FIG. 7. In an example embodiment, the face 12a of the target cellular structure 12 is scanned using the inspecting device 16 (step O1) and the target cell parameters are represented in numerical values (step O2). Then, the target cell parameters are input into the neural network 28 (step O3) and the neural network 28 yields an output value corresponding to the target cellular structure 12 based on the cell parameters obtained by scanning the face 12a (step O4).

A cellular structure 12 provided to help the neural network 28 detect the relationship during the learning mode can be characterized as a 'sample' cellular structure 12 that is used as a dummy while a cellular structure 12 the strength of which the neural network 28 attempts to predict during the predicting mode can be characterized as a 'target' cellular structure 12. Moreover, the features of the cellular structure 12, such as the face 12a, the cells 12b or the parameters, can also be characterized as 'sample' or 'target' in the same manner.

Figure 8:
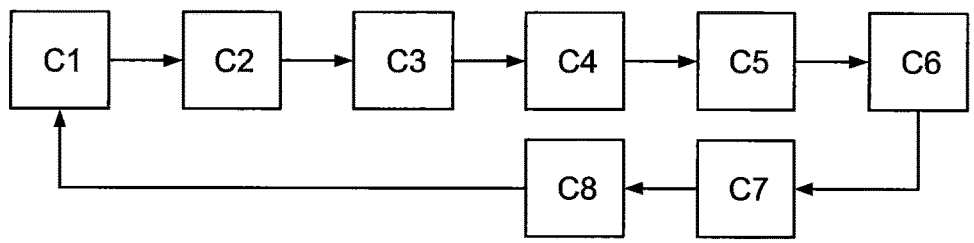
FIG. 8 is a flow chart representing multiple operating steps during a correcting mode of the system.

Furthermore, the system 10 may also include a correcting mode (FIG. 8) in which, after the neural network 28 has detected a relationship between the strength parameter and the cell parameters based on the sample database, the neural network 28 verifies a reliability of the relationship using a pool of target cellular structures 12. In an example embodiment, the inspecting device 16 scans the face 12a of a target cellular structure 12 (step C1) and represents the target cell parameters with numerical values (step C2). The target cell parameters are input into the neural network 28 (step C3) and the neural network 28 yields an output value based on the target cell parameters (step C4). The strength parameter of the target cellular structure 12 is then measured using the aforementioned destruction process (step C5) and is input into the neural network 28 (step C7). The neural network 28 verifies whether the output value is a reliable indicator of the strength of the target cellular structure 12 through comparison with the strength parameter and adjusts the relationship correcting any present discrepancy (step C8). For example, the adjustment of the relationship may be conducted by changing the weights stored at the synapses 34 of the neural network 28. Thereafter, these steps are repeated for a plurality of target cellular structures 12. It may be possible to first form a target database containing the cell parameters and the strength parameter from a pool of target cellular structures 12 and then to provide the parameters to the neural network 28 for necessary adjustment of the relationship.

It will be apparent to those skilled in the art that various modifications and variations can be made without departing from the spirit and scope of the claimed invention.

What is claimed is:

1. A method of using a neural network to generate a model to predict an indicator of an isostatic strength of a ceramic honeycomb cellular structure, the method comprising:
   inspecting the arrangement of sample cells of ceramic honeycomb cellular structures of respective sample cellular structures using an inspecting device and representing the arrangement of sample cells with numerically-defined sample cell parameters;
   destroying each of the sample ceramic cellular structures by applying force on respective sample cellular structures while measuring a sample strength parameter representing a maximum force that the sample cellular structure can endure prior to destruction;
   storing in a storage medium the sample cell parameters and the sample strength parameter corresponding to the sample cellular structures as a sample database;
   detecting a plurality of relationships between the sample strength parameter and the sample cell parameters in the sample database using a neural network;
   manufacturing a plurality of ceramic honeycomb cellular structures including a target cellular structure comprising an arrangement of target cells;
   generating a plurality of neural net models, using the neural network, based at least in part on the respective relationships between the sample strength parameter and the sample cell parameters, each neural net model having a different set of weights for each of a plurality of synapses in the respective neural net model based on the respective relationship between the sample strength parameter and the sample cell parameters;
   selecting the most accurate neural net model from the plurality of neural net models to be used to predict the indicator of the isostatic strength of the target cellular structure;
   non-destructively predicting the indicator of the isostatic strength of the target cellular structure by:
      inspecting the arrangement of target cells using the inspecting device;
      representing the arrangement of target cells with numerically defined target cell parameters;
      inputting the target cell parameters into the neural network; and
      generating an output from the neural network based on the target cell parameters by processing the target cell parameters using the most accurate neural net model that is selected from the plurality of neural net models, the output being indicative of the isostatic strength of the target cellular structure.

2. The method of claim 1, wherein the target cell parameters include one or more of outer skin shape, outer skin thickness, cell location, cell corner angle, horizontal cell pitch, vertical cell pitch, horizontal wall thickness, vertical wall thickness, horizontal wall bow and vertical wall bow.

3. The method of claim 1, further comprising inspecting the arrangement of target cells using the inspecting device of a plurality of target cellular structures, each target cellular structure comprising an arrangement of target cells, and non-destructively predicting an indicator of an isostatic strength of each target cellular structure by: representing the arrangement of target cells with numerically defined target cell parameters, inputting the target cell parameters into the neural network; and generating an output from the neural network based on the target cell parameters, the output being indicative of an isostatic strength of the target cellular structure; and determining a reliability of the output by comparing the outputs with the target strength parameters in the target database.

4. The method of claim 1, wherein the output is pass or fail.

5. The method of claim 1, wherein the output is a numerical prediction of the strength of the target cellular structure.

6. The method of claim 1 wherein the inspecting comprises scanning a face of the cellular structures by taking composite line images of the face.

7. The method of claim 1 further comprising capturing images of the cellular structures by a camera.

8. The method of claim 1 further comprising moving the cellular structures on a conveyor during the inspecting.

9. The method of claim 1 further comprising moving the cellular structures and illuminating the cellular structures.

10. The method of claim 1 wherein the sample cellular structures crack or implode during the destroying.

11. The method of claim 1, further comprising:
   destroying the target cellular structure by applying force on the target cellular structure while measuring a target strength parameter representing a maximum force that the target cellular structure can endure prior to destruction;
   comparing the target strength parameter and the indicator of the isostatic strength of the target cellular structure to determine a discrepancy between the target strength parameter and the indicator of the isostatic strength of the target cellular structure; and
   adjusting the most accurate neural net model to correct the discrepancy.

12. The method of claim 11, wherein adjusting the most accurate neural net model comprises:
   changing the set of weights for one or more of the synapses in the most accurate neural net model to correct the discrepancy.

13. The method of claim 1, wherein the sample cell parameters include one or more of outer skin shape, outer skin thickness, cell location, horizontal wall thickness, vertical wall thickness, horizontal wall bow, or vertical wall bow.

14. A method of non-destructively predicting an indication of isostatic strength of a target ceramic honeycomb cellular structure, the target cellular structure comprising an arrangement of target cells, the method comprising:
   moving the target cellular structure on a conveyor;

scanning the arrangement of target cells using an inspecting device;
representing the arrangement of target cells with numerically defined target cell parameters;
inputting the target cell parameters into a neural network, wherein the neural network comprises a sample database obtained by (i) inspecting a pool of sample ceramic cellular structures and respective arrangements of sample cells thereof, (ii) representing the arrangement of sample cells with numerically-defined sample cell parameters, and (iii) destroying the sample cellular structures by applying force on respective sample cellular structures while measuring a sample strength parameter representing a maximum force that each sample cellular structure can endure prior to destruction,
    wherein the neural network is configured to detect a plurality of relationships between the sample strength parameter and the sample cell parameters in the sample database,
    wherein the neural network is configured to generate a plurality of neural net models based at least in part on the respective relationships between the sample strength parameter and the sample cell parameters, each neural net model having a different set of weights for each of a plurality of synapses in the respective neural net model based on the respective relationship between the sample strength parameter and the sample cell parameters, and
    wherein the neural network is configured to select the most accurate neural net model from the plurality of neural net models to be used to predict the indicator of the isostatic strength of the target cellular structure; and
generating an output based on the target cell parameters by processing the target cell parameters using the most accurate neural net model that is selected from the plurality of neural net models, wherein the output is indicative of the isostatic strength of the target cellular structure.

15. The method of claim 14 wherein the sample cell parameters and the sample strength parameter corresponding to the sample cellular structures are stored in a storage medium.

16. The method of claim 14 further comprising illuminating the target cellular structure while the cellular structure is being moved on the conveyor.

17. The method of claim 14, wherein the sample cell parameters include one or more of outer skin shape, outer skin thickness, cell location, horizontal wall thickness, vertical wall thickness, horizontal wall bow, or vertical wall bow.

* * * * *